(12) United States Patent
Park et al.

(10) Patent No.: US 11,497,454 B2
(45) Date of Patent: Nov. 15, 2022

(54) APPARATUS AND METHOD FOR ESTIMATING BIO-INFORMATION

(71) Applicant: SAMSUNG ELECTRONICS CO., LTD., Suwon-si (KR)

(72) Inventors: Chang Soon Park, Chungju-si (KR); Ui Kun Kwon, Hwaseong-si (KR); Seung Keun Yoon, Seoul (KR); Dae Geun Jang, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 538 days.

(21) Appl. No.: 16/359,597

(22) Filed: Mar. 20, 2019

(65) Prior Publication Data

US 2020/0037963 A1   Feb. 6, 2020

(30) Foreign Application Priority Data

Aug. 1, 2018   (KR) .......................... 10-2018-0089786

(51) Int. Cl.
*A61B 5/02* (2006.01)
*A61B 5/00* (2006.01)
*A61B 5/0205* (2006.01)

(52) U.S. Cl.
CPC .......... *A61B 5/7282* (2013.01); *A61B 5/0205* (2013.01); *A61B 5/74* (2013.01)

(58) Field of Classification Search
CPC ....... A61B 5/7282; A61B 5/0205; A61B 5/74; A61B 5/681; A61B 5/7239; A61B 5/02116; A61B 5/02125; A61B 5/02007; A61B 5/0059; A61B 5/72; A61B 5/7275; A61B 5/7235; A61B 5/0075; A61B 5/021
See application file for complete search history.

(56) References Cited

U.S. PATENT DOCUMENTS

| | | | |
|---|---|---|---|
| 8,758,259 B2 | 6/2014 | Suzuki | |
| 9,131,859 B2 | 9/2015 | Sawanoi et al. | |
| 2003/0036685 A1 | 2/2003 | Goodman | |
| 2010/0081947 A1 | 4/2010 | Suzuki | |
| 2011/0021927 A1 | 1/2011 | Sawanoi et al. | |

(Continued)

FOREIGN PATENT DOCUMENTS

| | | |
|---|---|---|
| EP | 3 272 279 A2 | 1/2018 |
| EP | 3 295 869 A1 | 3/2018 |

(Continued)

OTHER PUBLICATIONS

Communication dated Nov. 19, 2019 issued by the European Patent Office in counterpart European patent Application No. 19174420.0.

(Continued)

*Primary Examiner* — Andrey Shostak
(74) *Attorney, Agent, or Firm* — Sughrue Mion, PLLC

(57) ABSTRACT

An apparatus for estimating bio-information is disclosed. The bio-information estimating apparatus includes: a sensor configured to measure a bio-signal; and a processor configured to obtain one or more characteristic points, related to one or more pulse waveform components constituting the bio-signal, based on a differential signal of the bio-signal, and to estimate bio-information based on the obtained one or more characteristic points.

15 Claims, 17 Drawing Sheets

(56) References Cited

U.S. PATENT DOCUMENTS

| | | | |
|---|---|---|---|
| 2012/0029363 A1* | 2/2012 | Lund | A61B 5/02108 |
| | | | 600/485 |
| 2012/0215275 A1 | 8/2012 | Wenzel et al. | |
| 2013/0079657 A1* | 3/2013 | Ochs | A61B 5/7235 |
| | | | 600/529 |
| 2013/0324859 A1 | 12/2013 | Park et al. | |
| 2017/0156609 A1 | 6/2017 | Yuan | |
| 2017/0238816 A1 | 8/2017 | Nakazawa et al. | |
| 2017/0258436 A1* | 9/2017 | Kj R Thing Riknagel | |
| | | | A61B 5/6833 |
| 2017/0296083 A1 | 10/2017 | Cardenas et al. | |
| 2018/0010062 A1 | 1/2018 | Guiducci et al. | |
| 2018/0020990 A1 | 1/2018 | Park et al. | |
| 2018/0078215 A1 | 3/2018 | Park et al. | |

FOREIGN PATENT DOCUMENTS

| | | |
|---|---|---|
| JP | 2009-219623 A | 10/2009 |
| JP | 5336803 B2 | 8/2013 |
| JP | 2016-220886 A | 12/2016 |
| KR | 10-1298838 B1 | 8/2013 |
| KR | 10-1503604 B1 | 3/2015 |
| KR | 10-2016-0000810 A | 1/2016 |
| KR | 10-2018-0010062 A | 1/2018 |

OTHER PUBLICATIONS

Yoon et al., "Nonconstrained Blood Pressure Measurement by Photoplethysmography", Journal of the Optical Society of Korea, vol. 10, No. 2, Jun. 2006, pp. 91-95, 5 pages total.

Millasseau et al., "The Vascular Impact of Aging and Vasoactive Drugs: Comparison of Two Digital Volume Pulse Measurements", American Journal of Hypertension, vol. 16, No. 6, Jun. 2003, pp. 467-472, 6 pages total.

Baruch et al., "Validation of the pulse decomposition analysis algorithm using central arterial blood pressure", BioMedical Engineering OnLine, Jul. 2014, pp. 1-19.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2018-0089786, filed on Aug. 1, 2018, in the Korean Intellectual Property Office, the entire disclosure of which is incorporated herein by reference for all purposes.

BACKGROUND

1. Field

Apparatuses and methods consistent with exemplary embodiments relate generally to an apparatus and a method for estimating bio-information such as blood pressure, and more particularly to technology for extracting pulse waveform components of a bio-signal to be used for estimation of bio-information.

2. Description of the Related Art

With an aging population, soaring medical costs, and a lack of medical personnel for specialized medical services, research is being actively conducted on information technology (IT)-medical convergence technologies, in which IT technology and medical technology are combined. Particularly, monitoring of the health condition of the human body is not limited to places such as hospitals, but is expanding to mobile healthcare fields that may monitor a user's health condition anywhere and anytime in daily life at home or office. Typical examples of bio-signals, which indicate the health condition of individuals, include an electrocardiography (ECG) signal, a photoplethysmogram (PPG) signal, an electromyography (EMG) signal, and the like, and various bio-signal sensors are being developed to measure these signals in daily life. Particularly, the PPG sensor may estimate blood pressure of a human body by analyzing a pulse waveform which reflects a condition of the cardiovascular system and the like.

Studies on the PPG signal show that the entire PPG signal is a superposition of propagation waves starting from the heart toward the distal end portions of the body and reflection waves returning back from the distal end portions. Further, it has been known that information for estimating blood pressure may be obtained by extracting various features related to the propagation waves or the reflection waves.

SUMMARY

One or more exemplary embodiments provide an apparatus and a method for accurately estimating bio-information by extracting a characteristic point having a high correlation with blood pressure.

According to an aspect of an exemplary embodiment, there is provided an apparatus for estimating bio-information. The apparatus includes a sensor configured to measure a bio-signal; and a processor configured to obtain one or more characteristic points, related to one or more pulse waveform components constituting the bio-signal, based on a differential signal of the bio-signal, and to estimate bio-information based on the obtained one or more characteristic points.

The processor may obtain an internally dividing point between a first point and a second point, the first point and the second point being selected from a first local minimum point related to a specific pulse waveform component and adjacent local maximum points preceding or following the first local minimum point in the differential signal, and obtain a characteristic point related to the specific pulse waveform component based on the obtained internally dividing point.

The processor may obtain a time value of the internally dividing point as a time value of the characteristic point from the differential signal, and obtain an amplitude value, corresponding to the time value of the internally dividing point, as an amplitude value of the characteristic point from the bio-signal.

The processor may obtain, as the internally dividing point, a middle point between a time value of the first point and a time value of the second point.

The processor may apply a weighted value to each of time values of the first point and the second point, and obtain the internally dividing point based on a result of applying the weighted value.

The processor may apply the weighted value to each of the time values based on at least one of differential signal strength of each of the first point and the second point, and an amplitude value of the bio-signal which corresponds to each of the time values of the first point and the second point.

The processor may select the first local minimum point as the first point, and any one of the adjacent local maximum points as the second point, and obtains the internally dividing point between the first point and the second point based on a difference in differential signal strength between the first point and the second point, and a difference in differential signal strength between a second local minimum point, which is different from the first local minimum point and adjacent to the second point, and the second point.

The processor may select the first point and the second point based on a sequence of pulse waveform components constituting the bio-signal.

The processor may, in obtaining a characteristic point related to a first pulse waveform component of the bio-signal, select a third local minimum point of the differential signal as the first point, and any one of adjacent local maximum points preceding or following the third local minimum point as the second point, the third local minimum point being a local minimum point that firstly appears in the differential signal.

The processor may, obtaining a characteristic point related to an n-th (n≥2, n being an integer) pulse waveform component of the bio-signal, respectively select, as the first point and the second point, local maximum points respectively preceding and following a local minimum point that appears n-th in the differential signal.

The processor may extract a feature by combining one or more of the obtained one or more characteristic points related to the one or more pulse waveform components, and estimate the bio-information based on the extracted feature.

The sensor may include a light source configured to emit light onto an object; and a detector configured to detect light scattered from the object.

The bio-information may include one or more of blood pressure, vascular age, arterial stiffness, aortic pressure waveform, stress index, and degree of fatigue.

The apparatus may further include an output part configured to output a processing result of the processor.

According to an aspect of an exemplary embodiment, there is provided a method of estimating bio-information. The method includes measuring a bio-signal; and obtaining one or more characteristic points, related to one or more pulse waveform components constituting the bio-signal, based on a differential signal of the bio-signal; and estimating bio-information based on the obtained one or more characteristic points.

The obtaining may include selecting a first point and a second point from a first local minimum point related to a specific pulse waveform component and adjacent local maximum points preceding or following the first local minimum point in the differential signal; obtaining an internally dividing point between the first point and the second point; and obtaining a characteristic point related to the specific pulse waveform component based on the obtained internally dividing point.

The obtaining the internally dividing point may include obtaining, as the internally dividing point, a middle point between a time value of the first point and a time value of the second point.

The obtaining the internally dividing point may include applying a weighted value to each of time values of the first point and the second point, and obtaining the internally dividing point based on a result of the applying the weighted value.

The obtaining the internally dividing point based on the result of the applying the weighted value may include applying the weighted value to each of the time values based on at least one of a differential signal strength of each of the first point and the second point, and an amplitude value of the bio-signal which corresponds to each of the time values of the first point and the second point.

The selecting the first point and the second point may include selecting the first local minimum point as the first point, and selecting any one of the adjacent local maximum points as the second point. The obtaining the internally dividing point may include obtaining the internally dividing point between the first point and the second point based on a difference in differential signal strength between the first point and the second point, and a difference in differential signal strength between a second local minimum point, which is different from the first local minimum point and adjacent to the second point, and the second point.

The selecting the first point and the second point may include selecting the first point and the second point based on a sequence of pulse waveform components constituting the bio-signal.

The selecting the first point and the second point may include, in obtaining a characteristic point related to a first pulse waveform component of the bio-signal, selecting a third local minimum point of the differential signal as the first point, and any one of adjacent local maximum points preceding or following the third local minimum point as the second point, the third local minimum point being a local minimum point that firstly appears in the differential signal.

The selecting the first point and the second point may include, in obtaining a characteristic point related to an n-th (n≥2, n being an integer) pulse waveform component of the bio-signal, respectively selecting, as the first point and the second point, local maximum points respectively preceding and following a local minimum point that appears n-th in the differential signal.

The estimating may include: extracting a feature by combining one or more of the obtained one or more characteristic points related to the one or more pulse waveform components; and estimating the bio-information based on the extracted feature.

The method may further include outputting an estimation result of the bio-information.

According to an aspect of an exemplary embodiment, there is provided an apparatus for estimating bio-information. The apparatus may include a communicator configured to receive a bio-signal from an external device; a processor configured to obtain one or more characteristic points, related to one or more pulse waveform components constituting the bio-signal, based on a differential signal of the received bio-signal, and to estimate bio-information based on the obtained one or more characteristic points.

The external device may include at least one of a bio-signal measuring sensor, a smartphone, a tablet personal computer (PC), and a wearable device.

The processor may obtain an internally dividing point between a first point and a second point, which are selected from a first local minimum point related to a specific pulse waveform component and adjacent local maximum points preceding or following the first local minimum point in the differential signal, and obtain a characteristic point related to the specific pulse waveform component based on the obtained internally dividing point.

The apparatus may further include an output part configured to output at least one of the estimated bio-information and a change trend graph illustrating a change trend of the bio-information.

In response to at least one of a user selection of the estimated bio-information and a user selection of a time point of the change trend graph, the output part may display at least one of a bio-signal related to the selected bio-information, the differential signal, a pulse waveform, and a characteristic point related to the pulse waveform.

BRIEF DESCRIPTION OF THE DRAWINGS

The above and/or other aspects will become apparent and more readily appreciated by describing certain exemplary embodiments with reference to the accompanying drawings, in which.

DETAILED DESCRIPTION

Figure 1:
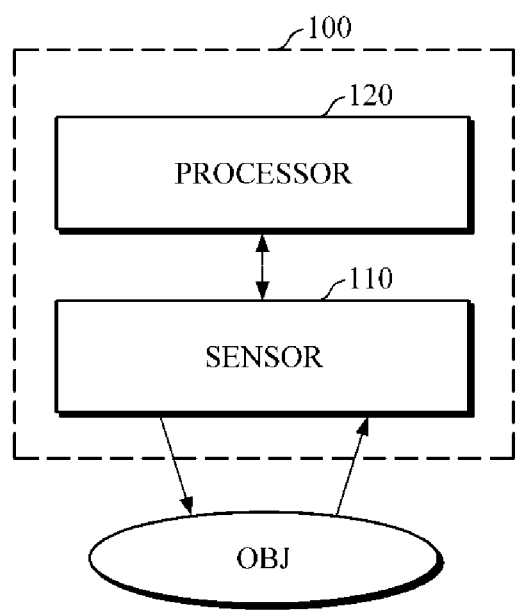
FIG. 1 is a block diagram illustrating a bio-information estimating apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail. The relative size and depiction of these elements may be exaggerated for clarity, illustration, and convenience.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, exemplary embodiments of a bio-information estimating apparatus and a bio-information estimating method will be described in detail with reference to the accompanying drawings.

FIG. 1 is a block diagram illustrating a bio-information estimating apparatus according to an exemplary embodiment. The bio-information estimating apparatus 100 may be embedded in a terminal, such as a smartphone, a tablet personal computer (PC), a desktop computer, a laptop computer, and the like, or in a wearable device that may be worn on an object OBJ. Examples of the wearable device may include a wristwatch-type wearable device, a bracelet-type wearable device, a wristband-type wearable device, a ring-type wearable device, a glasses-type wearable device, a hairband-type wearable device, or the like, but the wearable device is not limited thereto. For example, the wearable device may be embedded in a medical device manufactured for use in medical institutions to measure and analyze bio-information.

Referring to FIG. 1, the bio-information estimating apparatus 100 includes a sensor 110 and a processor 120.

The sensor 110 may measure a bio-signal from the object OBJ. The bio-signal may be a pulse wave signal including a photoplethysmogram (PPG) signal. However, the bio-signal is not limited thereto, and may include various bio-signals, such as an electrocardiography (ECG) signal, a photoplethysmogram (PPG) signal, an electromyography (EMG) sensor, and the like, which may be modeled by the sum of a plurality of waveform components. The object OBJ may be a body part which comes into contact with or is adjacent to the sensor 110, and may be a body part where pulse waves may be easily measured. For example, the object OBJ may be an area on the wrist that is adjacent to the radial artery or a human skin area through which veins or capillaries pass, but the object is not limited thereto, and may be peripheral body portions, such as fingers, toes, and the like, which have a high density of blood vessels.

The sensor 110 may include a light source and a detector. The light source may emit light onto the object OBJ, and the detector may detect light scattered or reflected from the object OBJ. The light source may include a light emitting diode (LED), a laser diode (LD), a fluorescent body, and the like, and may include one array or two or more arrays. The detector may include one or more pixels, each of which includes a photo diode, a photo transistor (PTr), and the like, which detects light and converts the detected light into an electric signal.

The processor 120 may be electrically connected to the sensor 110. The processor 120 may control the sensor 110 in response to a request for estimating bio-information, and may receive a bio-signal measured by the sensor 110. The request for estimating bio-information may be input by a user, or may be generated at predetermined intervals. Upon receiving a bio-signal from the sensor 110, the processor 120 may perform preprocessing such as filtering for reducing noise, amplification of the bio-signal, conversion of the bio-signal to a digital signal, and the like.

The processor 120 may estimate bio-information based on the bio-signal received from the sensor 110. In this case, the bio-information may include blood pressure, vascular age, arterial stiffness, aortic pressure waveform, stress index, degree of fatigue, and the like, but is not limited thereto.

For example, the processor 120 may obtain a differential signal of the received bio-signal, and may obtain a characteristic point, related to one or more pulse waveform components constituting the bio-signal, based on the obtained differential signal. The differential signal may be a secondary differential signal, but is not limited thereto.

For example, the processor 120 may detect a local minimum point and a local maximum point from the secondary differential signal, and may obtain a characteristic point, related to individual pulse waveform components constituting the bio-signal, by using the detected local minimum point and local maximum point. Each local minimum point detected from the secondary differential signal may be related to each pulse waveform component which causes the bio-signal to have an upward convex waveform.

The processor 120 may obtain, as a characteristic point, a point of a bio-signal waveform which corresponds to each local minimum point detected from the secondary differential signal. Alternatively, the processor 120 may obtain an internally dividing point by using the detected local minimum point and local maximum point, and may obtain a point of the bio-signal waveform, which corresponds to the obtained internally dividing point, as a characteristic point. In this manner, even when the bio-signal waveform is unstable due to a non-ideal environment such as motion noise, light noise, sleep, and the like, the processor 120 may accurately obtain a characteristic point.

Based on a sequence of pulse waveform components of the bio-signal and/or characteristics of the bio-signal waveform, the processor 120 may determine a method of selecting a local minimum point, a local maximum point, an internally dividing point, and the like, which are references for obtaining a characteristic point, and/or a method of selecting two points which are references for obtaining an internally dividing point. For example, according to the sequence of pulse waveform components to be obtained, the processor 120 may select, as two points for obtaining an internally dividing point, a local minimum point and a local maximum point adjacent to the local minimum point, either preceding or following the local minimum point, or select, as two points for obtaining an internally dividing point, a preceding local maximum point and a following local maximum point adjacent to the local minimum point.

Upon obtaining a characteristic point for one or more pulse waveforms, the processor 120 may extract a feature by combining time and amplitude information of the characteristic point for each pulse waveform, and may estimate bio-information by using the extracted feature. In this case, the processor 120 may estimate bio-information by applying a pre-generated estimation model. The bio-information estimation model may be a linear or non-linear function.

Figure 2:
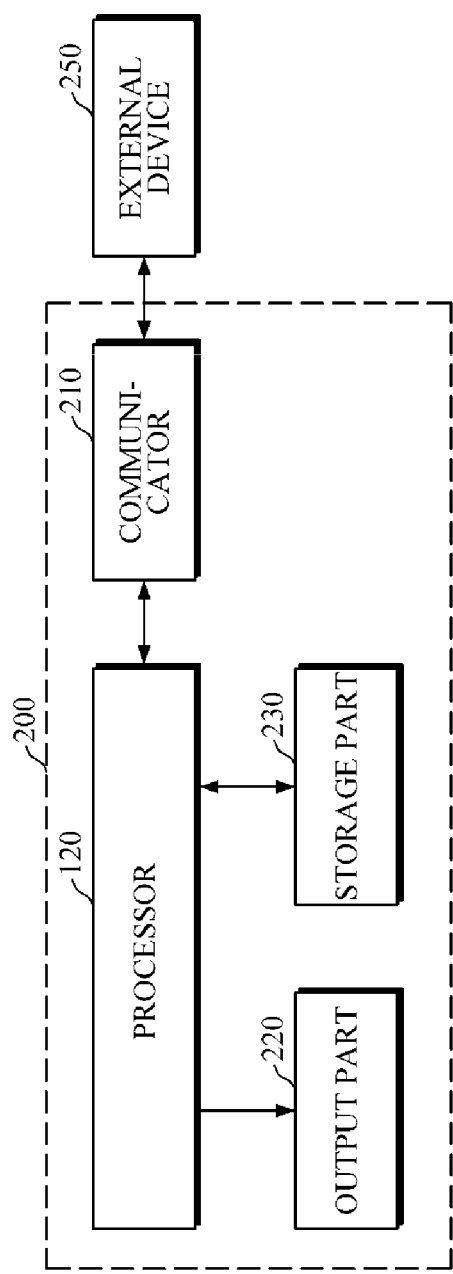
FIG. 2 is a block diagram illustrating a bio-information estimating apparatus according to another embodiment.

FIG. 2 is a block diagram illustrating a bio-information estimating apparatus according to another exemplary embodiment.

Referring to FIG. 2, the bio-information estimating apparatus 200 includes a processor 120, a communicator 210, an output part 220, and a storage part 230.

The communicator 210 may communicate with an external device 250 by connecting to a communication network using a communication technique. The communicator 210 may receive a bio-signal from the external device 250, and may transmit the received bio-signal to the processor 120. In an exemplary embodiment, no sensor for measuring a bio-signal may be included, such that the bio-information estimating apparatus 200 may be manufactured in a compact size, and may be mounted in various information processing devices. Examples of the external device 250 may include a smartphone, a tablet PC, a laptop computer, a desktop computer, and a wearable device, but the external device 250 is not limited thereto. Further, the external device 250 may be a bio-signal measuring sensor, in which case the communicator 210 may communicate with the sensor directly by wire or wirelessly.

Although a sensor for measuring a bio-signal is not illustrated in FIG. 2, the bio-information estimating apparatus 200 may include the sensor depending on an embodiment. In this case, under the control of the processor 120 or at the request of the external device 250, the bio-information estimating apparatus 200 may selective obtain a bio-signal. For example, the bio-information estimation apparatus 200 may obtain a bio-signal by receiving a bio-signal from the external device 250 or by directly driving the sensor.

In this case, the communicator 210 may perform communication by using a communication technique such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WiFi communication, mobile communications, and the like. However, this is merely exemplary and is not intended to be limiting.

Upon receiving a bio-signal, the processor 120 may obtain a characteristic point by analyzing the received bio-signal, and may extract a feature, which is to be used for estimating bio-information, by using the obtained characteristic point. In this case, when a bio-signal waveform is non-ideal and unstable, the processor 120 may obtain an internally dividing point by using local minimum points and local maximum points of a secondary differential signal, and may obtain a characteristic point of the bio-signal based on the internally dividing point. Further, the processor 120 may estimate bio-information by using the extracted feature and an estimation model.

The output part 220 may output and provide a bio-signal and/or an estimation result of bio-information to a user. For example, the output part 220 may output the estimated bio-information or a graph illustrating a change trend of bio-information. In this case, in response to a user's selection of any one bio-information item from the change trend graph of bio-information, the processor 120 may read detailed information related to the selected bio-information, e.g., a bio-signal, a differential signal, a pulse waveform, a characteristic point, and the like, from the storage part 230, and may output the read information through the output part 220.

The output part 220 may output the information by various visual methods using a display module, or by non-visual methods through voice, tactile sensation, vibration, and the like using a speaker, a haptic module, and the like. For example, based on information whether estimated blood pressure of a user is normal, the output part 220 may display the blood pressure by adjusting a font color or a font style, and the like. Alternatively, the output part 220 may display the estimated blood pressure by a non-visual method through voice, or by changing vibration, tactile sensation, and the like based on abnormality of blood pressure. In addition, in the case where the estimated blood pressure is not normal, the output part 220 may output the blood pressure along with warning information, and depending on an embodiment, may also output guide information, including food information requiring attention, appropriate or inappropriate actions before measuring blood pressure, various types of additional information, and the like.

The storage part 230 may store reference information to be used for estimating bio-information, the obtained bio-signal, a differential signal, a local minimum point, a local maximum point, an internally dividing point, a characteristic point, a feature, an estimation result of bio-information, and the like. In this case, the reference information used for estimating bio-information may include user information, such as a user's age, gender, occupation, current health condition, and the like, estimation model information, and the like, but is not limited thereto.

The storage part 230 may include at least one storage medium of a flash memory type memory, a hard disk type memory, a multimedia card micro type memory, a card type memory (e.g., a Secure Digital (SD) memory, an eXtreme Digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but the storage medium is not limited thereto.

The processor 120 may be connected to the communicator 210, the output part 220, and the storage part 230 through an internal bus, and may control the communicator 210, the output part 220, and the storage part 230. For example, the processor 120 may control the communicator 210 to transmit and receive various types of information with the external device 250. In addition, through the communicator 210, the processor 120 may store the received information in the storage part 230 and may obtain information used for estimating bio-information from the storage part 230. Further, the processor 120 may control the output part 220 to output a processing result.

Figure 3:
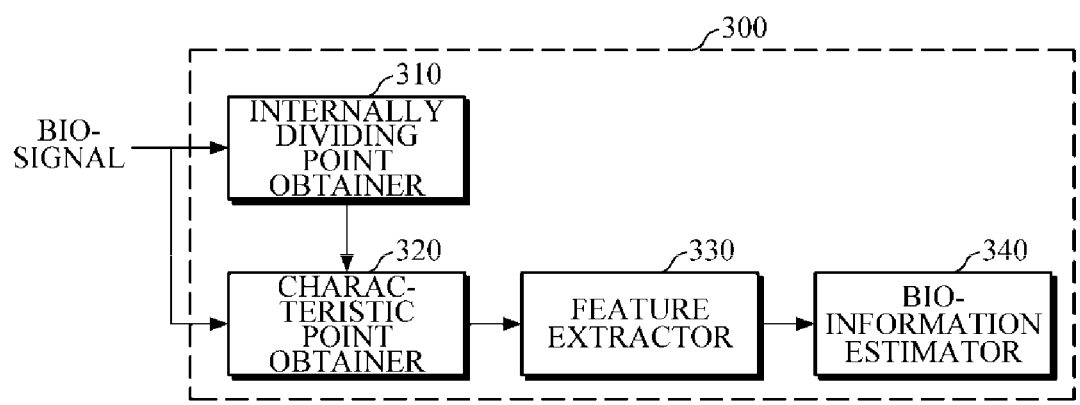
FIG. 3 is a block diagram illustrating a processor according to the embodiments of FIGS. 1 and 2.

FIG. 3 is a block diagram illustrating a processor according to the embodiments of FIGS. 1 and 2. FIGS. 4A to 4H are diagrams explaining an example of obtaining an internally dividing point from a bio-signal.

Figure 4A:
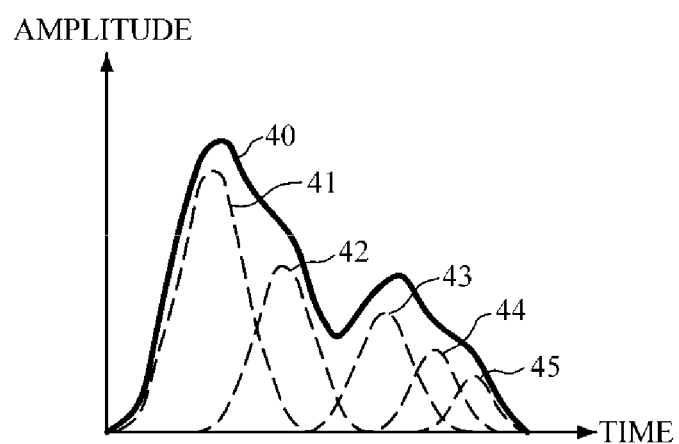
FIGS. 4A to 4H are diagrams explaining an example of obtaining an internally dividing point from a bio-signal.

Generally, the pulse wave signals, obtained from an object, are a superposition of propagation waves, starting from the heart toward the distal end portions of the body, and reflection waves returning back from the distal end portions. FIG. 4A illustrates an example of a pulse wave signal 40 formed by superposition of five pulse waveforms 41, 42, 43, 44, and 45. By obtaining points, related to the pulse waveforms 41, 42, 43, 44, and 45, as characteristic points from the pulse wave signal 40, and by properly combining time and amplitude information of the obtained characteristic points and the like, features having a high correlation with blood pressure may be extracted. Generally, pulse waveforms from the first pulse waveform up to the third pulse waveform are mainly used to estimate blood pressure. Pulse waveforms after the third pulse waveform may not be observed depending on individuals in some cases, and are difficult to find due to noise, or have a low correlation with estimation of blood pressure.

Referring to FIG. 3, the processor 300 includes an internally dividing point obtainer 310, a characteristic point obtainer 320, a feature extractor 330, and a bio-information estimator 340.

The internally dividing point obtainer 310 may obtain a differential signal (e.g., secondary differential signal) from a bio-signal, and may obtain a local minimum point and a local maximum point by detecting the obtained differential signal. Here, the local minimum point in an interval of a secondary differential signal refers to a specific point at which the secondary differential signal is observed to be reduced and then is increased past the specific point. In other words, the local minimum point refers to a point at which the second differential signal forms a downward convex shape. By contrast, the local maximum point in an interval of the secondary differential signal refers to a point at which the secondary differential signal forms an upward convex shape. In this case, an i-th local minimum point of the differential signal may be related to an i-th pulse waveform of the bio-signal, in which i≥1, and i is an integer.

Further, the internally dividing point obtainer 310 may select two points from among the detected local minimum points and local maximum points, and may obtain an internally dividing point between the selected two points. For example, the internally dividing point obtainer 310 may obtain, as an internally dividing point, a middle point on a time axis between the selected first point and second point, as represented by the following Equation 1. That is, the internally dividing point obtainer 310 may determine, as a time value of an internally dividing point, a median value between a time value of the first point and a time value of the second point.

$$T_{di} = \frac{T_{1i} + T_{2i}}{2} \quad \text{[Equation 1]}$$

Herein, $T_{di}$ denotes the time value of the internally dividing point related to an i-th pulse waveform component, and $T_{1i}$ and $T_{2i}$ denote the time values of the first point and the second point selected for obtaining the internally dividing point related to the i-th pulse waveform component.

In another example, the internally dividing point obtainer 310 may apply a weighted value to each of the time values of the first point and the second point, and may obtain an internally dividing point based on each of the time values to which the weighted value is applied, as represented by the following Equation 2.

$$T_{di} = \frac{a\ T_{1i} + b\ T_{2i}}{a + b} \quad \text{[Equation 2]}$$

Herein, $T_{di}$ denotes the time value of the internally dividing point related to the i-th pulse waveform component; $T_{1i}$ and $T_{2i}$ denote the time values of the first point and the second point selected for obtaining the internally dividing point related to the i-th pulse waveform component; and a and b denote weighted values respectively applied to the time values of each of the points. In this case, the weighted values a and b may be set based on the strength of each differential signal of the first point and the second point, or based on an amplitude value of a bio-signal corresponding to the time values of the first point and the second point.

The internally dividing point obtainer 310 may select two points from among local minimum points and local maximum points based on a sequence of pulse waveform components. For example, in order to obtain a characteristic point related to a first pulse waveform component of a bio-signal, the internally dividing point obtainer 310 may select a first local minimum point of a differential signal as a first point, and may select any one of adjacent local maximum points preceding or following the first local minimum point on the time axis, for example, a following local maximum point, as a second point. Alternatively, in order to obtain a characteristic point related to an n-th (n≥2, n being an integer) pulse waveform component of the bio-signal, the internally dividing point obtainer 310 may select local maximum points, preceding or following an n-th local minimum point, as the first point and the second point, but the characteristic point is not limited thereto.

The characteristic point obtainer 320 may obtain a characteristic point related to each pulse waveform component from the bio-signal based on the detected local minimum point and/or the internally dividing point. The characteristic point obtainer 320 may obtain, as the characteristic point related to pulse waveform components, each point of the bio-signal waveform which corresponds to the time of the local minimum point of the obtained differential signal and/or the time of the internally dividing point, and may obtain time and amplitude information of each characteristic point as information of each pulse waveform component.

Figure 4B:
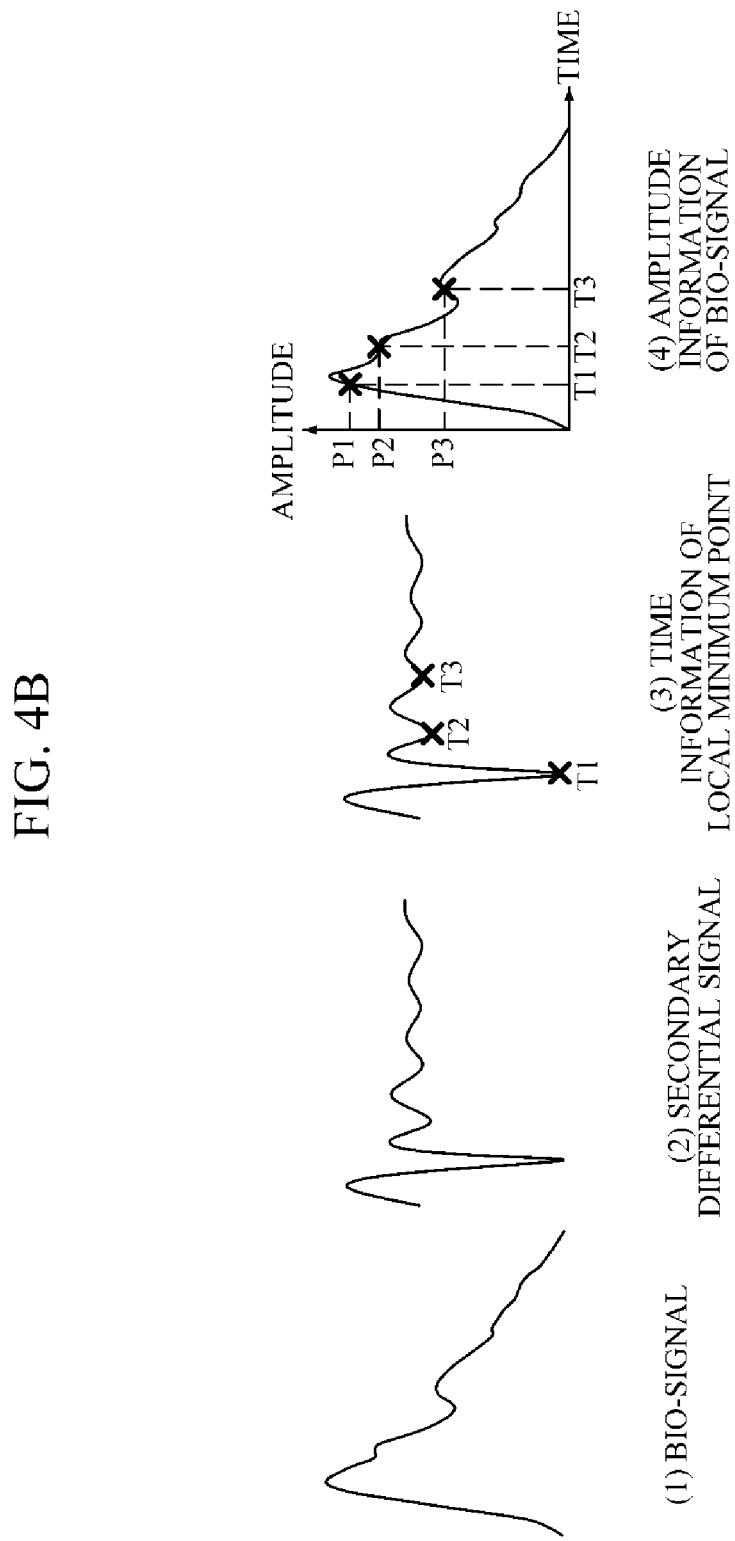

Referring to FIG. 4B, (1) once a bio-signal is obtained, (2) the internally dividing point 310 performs secondary differentiation of the obtained bio-signal to obtain a secondary differential signal, and (3) may detect local minimum points from the obtained secondary differential signal, to extract time values T1, T2, and T3 corresponding to a first, a second, and a third local minimum points. Then, (4) the characteristic point obtainer 320 may obtain, as characteristic points related to the first, second, and third pulse waveform components, each point of the bio-signal waveform corresponding to the time values T1, T2, and T3 of the local minimum points extracted by the internally dividing point obtainer 310, and may obtain information on the time values T1, T2, and T3 and amplitude values P1, P2, and P3 of the characteristic points as information of each pulse waveform component.

Figure 4C:
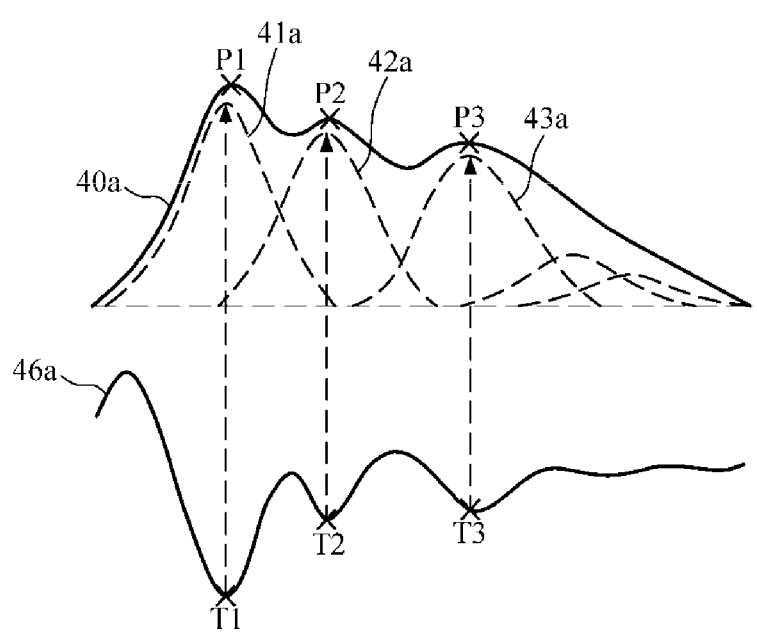

FIG. 4C illustrates an example of an ideal bio-signal 40a, in which individual waveform components 41a, 42a, and 43a may be easily identified even in a superposed waveform of the bio-signal 40a. Accordingly, in the case where the ideal bio-signal 40a is obtained, the internally dividing point 310 may extract the time values T1, T2, and T3 of the first, second, and third local minimum points from a secondary differential signal 46a, without separately performing operation to obtain an internally dividing point. The characteristic point obtainer 320 may obtain points, corresponding to each of the time values T1, T2, and T3 extracted by the internally dividing point obtainer 310, from the waveform of the bio-signal 40a as characteristic points of the first, second, and third pulse waveforms 41a, 42a, and 43a. In addition, the characteristic point obtainer 320 may obtain information on the time values T1, T2, and T3 and amplitude values P1, P2, and P3 as information of each pulse waveform component.

Figure 4D:
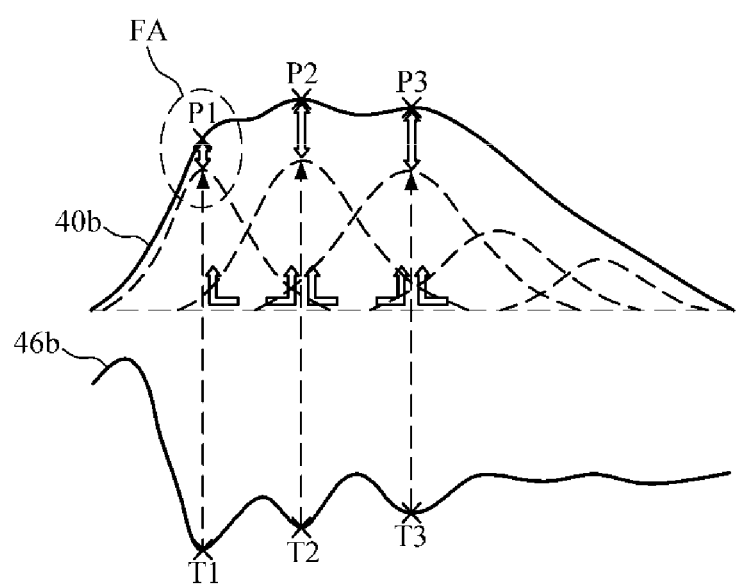
Figure 4E:
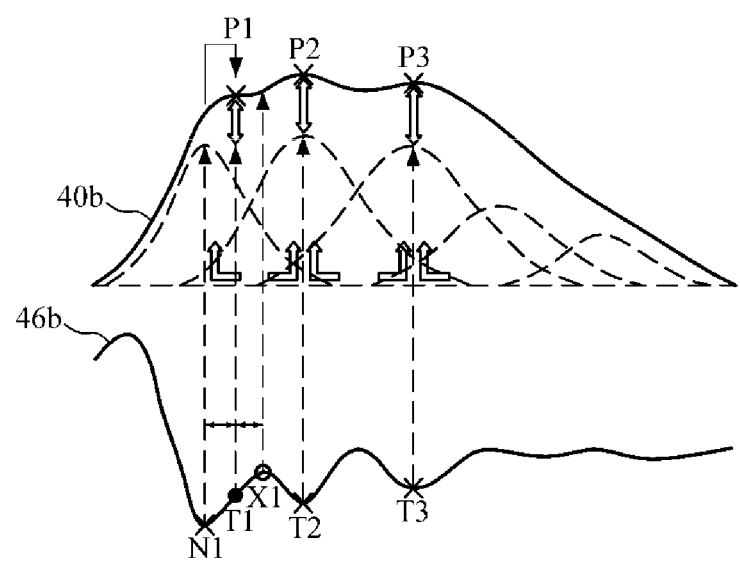

FIGS. 4D and 4E illustrate an example where individual waveform components are not easily identified but distorted in a superposed waveform of a bio-signal 40b. Referring to FIG. 4D, relative imbalance of a superposed amount of amplitudes occurs in an area near a point of the bio-signal 40b which corresponds to the time T1 of a first local minimum point of a secondary differential signal 46b. That is, there is no anterior interference in the amplitude P1 related to the first waveform component as compared to other waveform components, such that asymmetry in the direction of interference occurs, resulting in a smaller amplitude value P1 than intended. Under these circumstances, when bio-information is estimated using the time values T1, T2, and T3 and amplitude values P1, P2, and P3 obtained as illustrated in FIG. 4C, accuracy of estimating bio-information may be reduced.

Referring to FIG. 4E, under the circumstances of FIG. 4D, the internally dividing point obtainer 310 may obtain an internally dividing point to obtain a characteristic point related to the first pulse waveform. As illustrated therein, in order to obtain a characteristic point related to the first pulse waveform, the internally dividing point obtainer 310 may select a first local minimum point N1 of a secondary differential signal 46b as a first point, and may select a local maximum point X1, adjacent to the first local minimum point N1 on the right side thereof, as a second point. Further, the internally dividing point obtainer 310 may obtain an internally dividing point between the first point N1 and the second point X1 as described above. The characteristic point obtainer 320 may obtain a time value T1 and an amplitude value P1 related to the internally dividing point from a bio-signal 40b as a characteristic point of the first pulse waveform component. It can be seen that compared to FIG. 4D, the characteristic point of the first pulse waveform component is moved to the right, i.e., to a position adjacent to a first upward convex point of the bio-signal.

Figure 4F:
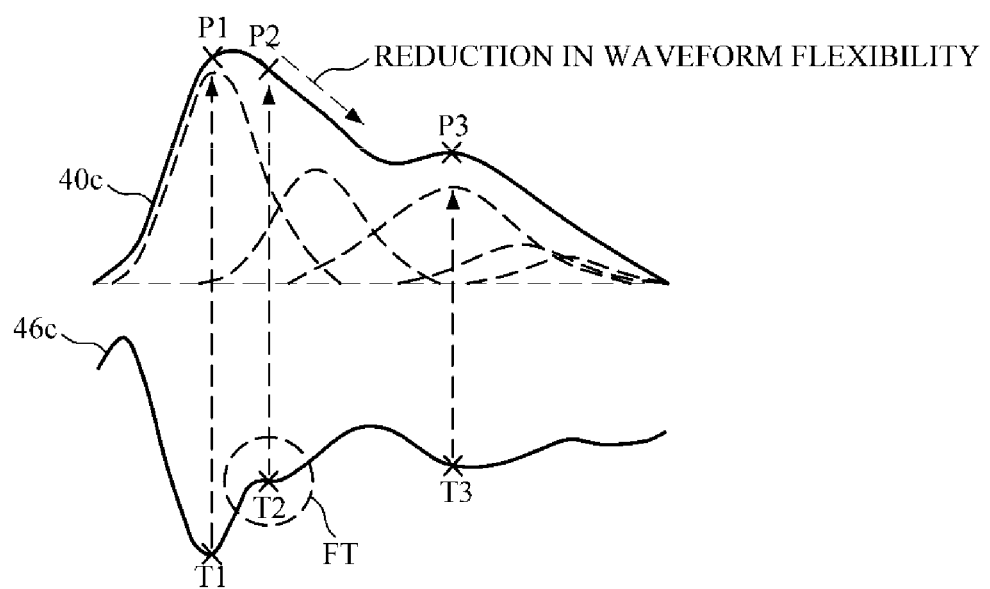
Figure 4G:
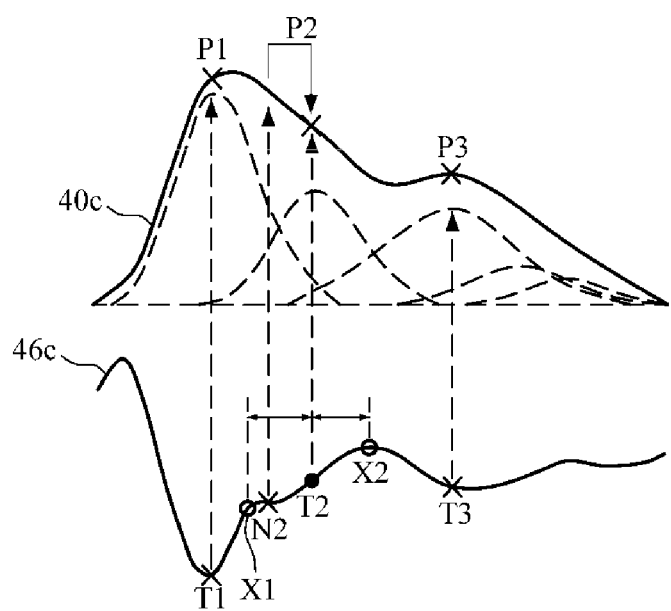

FIGS. 4F and 4G illustrate an example where waveform flexibility of a bio-signal 40c is relatively reduced. Referring to FIG. 4F, the flexibility is reduced at a point related to the second pulse waveform component in the bio-signal 40c, thereby increasing instability of the time value T2 in an area FT near the second local minimum point of a secondary differential signal 46c. As a result, the amplitude value P2 related to the second pulse waveform may be obtained at an incorrect location. Under these circumstances, when characteristic points are obtained as in the case of the ideal bio-signal illustrated in FIG. 4C, and bio-information is estimated using the time values T1, T2, and T3 and amplitude values P1, P2, and P3 obtained as illustrated in FIG. 4C, accuracy of estimating bio-information may be reduced.

Referring to FIG. 4G, under the circumstances of FIG. 4F, the internally dividing point obtainer 310 may obtain an internally dividing point to accurately obtain a characteristic point related to the second pulse waveform of the bio-signal 40c. As illustrated in FIG. 4G, in order to obtain a characteristic point related to the second pulse waveform, the internally dividing point obtainer 310 may select preceding or following local maximum points X1 and X2, adjacent to a second local minimum point N2 of the secondary differential signal 46c, as the first point and the second point respectively. Further, the internally dividing point obtainer 310 may obtain an internally dividing point between the first point X1 and the second point X2 as described above. In this case, the characteristic point obtainer 320 may obtain the time value T2 and the amplitude value P2 related to the internally dividing point from the bio-signal 40c as a characteristic point of the second pulse waveform component. It can be seen that compared to FIG. 4F, the characteristic point of the second pulse waveform component is moved to the right, i.e., to a position adjacent to the second pulse waveform component. Therefore, according to an exemplary embodiment, accuracy of estimating bio-information may be improved.

Figure 4H:
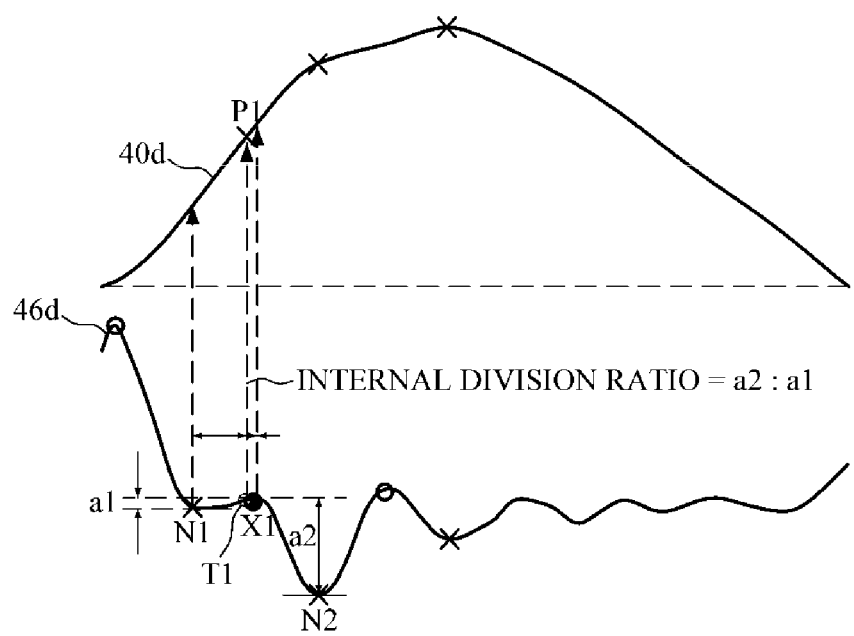

FIG. 4H is a diagram explaining another example of obtaining an internally dividing point by the internally dividing point obtainer 310. In order to obtain a characteristic point related to the first pulse waveform from a bio-signal 40d, the internally dividing point obtainer 310 may select the first local minimum point N1 of a differential signal 46d and the local maximum point X1, adjacent to the first local minimum point N1, as the first point and the second point respectively, and may internally divide the time between the first point N1 and the second point X1 at a predetermined ratio.

For example, the internally dividing point obtainer 310 may calculate a difference a1 in differential signal strength between the first point N1 and the second point X1, and a difference a2 in differential signal strength between the second point X1 and a second local minimum point N2 following the second point N1, and may obtain an internally dividing point by using the calculated values a1 and a2 as an internal division ratio between the first point N1 and the second point X1. The characteristic point obtainer 320 may obtain, as a characteristic point of the first pulse waveform, the time T1 of the obtained internally dividing point and the amplitude P1 of the bio-signal corresponding to the time.

Although FIG. 4H illustrates an example of obtaining an internally dividing point related to the first pulse waveform, the example may also be applied to the case of obtaining an internally dividing point related to the second and subsequent pulse waveforms following the first pulse waveform. For example, in order to obtain an internally dividing point related to the second pulse waveform, local maximum points adjacent to the second local minimum point may be selected as the first point and the second point, and a difference in the differential signal strength between the first point and the second local minimum point and a difference in the differential signal strength between the second point and the second local minimum point may be used as an internal division ratio between the first point and the second point.

In FIG. 4H, the difference in the differential signal strength between two points is used as an internal division ratio, but the internal division ratio is not limited thereto, and a difference in the amplitude value between two points may also be used.

Referring back to FIG. 3, the characteristic point obtainer 320 may obtain, as characteristic point information, various types of information in addition to the aforementioned characteristic points related to the local minimum point of the differential signal and/or the internally dividing point. For example, the characteristic point obtainer 320 may obtain, as additional characteristic point information, a specific interval of a bio-signal, a time and an amplitude at a point where an amplitude has a maximum value in a systolic blood pressure (SBP) interval, an entire area or a partial area of the bio-signal waveform, and the like.

Once characteristic points are extracted from the bio-signal, the feature extractor 330 may combine the extracted characteristic points to extract a feature for estimating bio-information, as represented by the following Equation 3. However, Equation 3 is merely exemplary, and characteristic point information itself or various combinations of two or more characteristic points may also be used.

$$f = \frac{P1 + P2}{P3} \quad \text{[Equation 3]}$$

Once the feature extractor 330 extracts a feature, the bio-information estimator 340 may estimate bio-information by using the extracted feature. For example, the bio-information estimator 340 may estimate blood pressure by applying the feature, for example, extracted by using the above Equation 3, to a blood pressure estimation equation as represented by the following Equation 4.

$$BP = A(f_1 + w f_2) + B \quad \text{[Equation 4]}$$

Herein, BP denotes an estimated blood pressure value, and A, w, and B denote any predefined coefficients.

Figure 5:
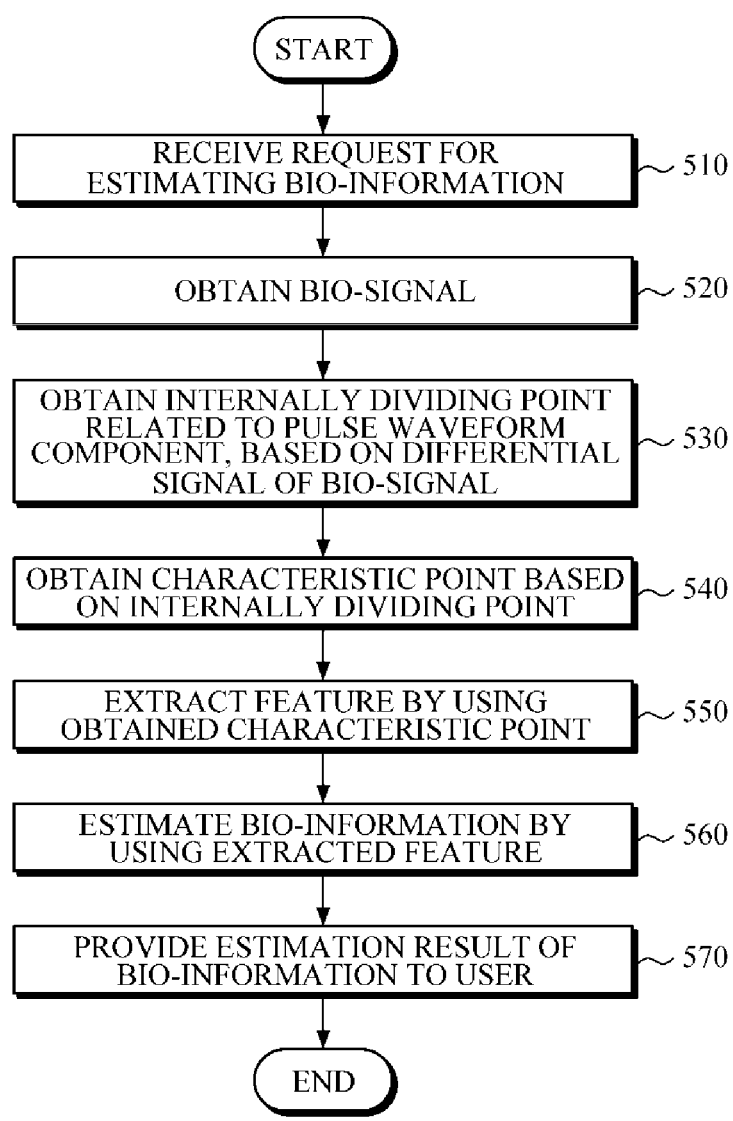
FIG. 5 is a flowchart illustrating a bio-information estimating method according to an embodiment.

FIG. 5 is a flowchart illustrating a bio-information estimating method according to an exemplary embodiment. The embodiment of FIG. 5 may be an example of a bio-information estimating method performed by any one of the bio-information estimating apparatuses 100 and 200 of FIG. 1 or 2, which is described above in detail, such that description thereof will be briefly made.

The bio-information estimating apparatus may receive a request for estimating bio-information in 510. The bio-information estimating apparatus may provide an interface which performs various interactions with a user. The user may transmit a request for estimating bio-information through the interface provided by the bio-information estimating apparatus. Alternatively, a request for estimating bio-information may be received from an external device. The request for estimating bio-information received form the external device may include a request for providing an estimation result of bio-information. In the case where the external device has an embedded algorithm for estimating bio-information, the request for estimating bio-information may also include a request for providing characteristic points or feature information. Examples of the external device may include a smartphone, a tablet PC, a laptop computer, a wearable device and the like which may be carried by a user.

Then, the bio-information estimating apparatus may obtain a bio-signal for estimating bio-information in 520. For example, in the case where a sensor is mounted in the bio-information estimating apparatus, the bio-information estimating apparatus may control a sensor to obtain a pulse wave signal from an object. Alternatively, in the case where no sensor for measuring a bio-signal is included, the bio-information estimating apparatus may receive a bio-signal from an external device.

Subsequently, the bio-information estimating apparatus may obtain an internally dividing point, related to pulse waveform components constituting the bio-signal, based on a differential signal of the obtained bio-signal in 530. For example, the bio-information estimating apparatus may detect a local minimum point and a local maximum point of a secondary differential signal, and may obtain an internally dividing point by using the detected local minimum point and local maximum point. As described above, in order to obtain a characteristic point related to a first pulse waveform component, the bio-information estimating apparatus may obtain an internally dividing point between the first local minimum point and an adjacent local maximum point. Additionally, in order to obtain a characteristic point related to pulse waveform components of the second and subsequent pulse waveforms following the first pulse waveform, the bio-information estimating apparatus may obtain an internally dividing point between two local maximum points adjacent to a local minimum point of the second and subsequent pulse waveforms.

Next, the bio-information estimating apparatus may obtain a characteristic point from the bio-signal based on the local minimum point obtained from the differential signal and/or the internally dividing point in 540. The bio-information estimating apparatus may obtain, as a characteristic point, a point corresponding to a time of the local minimum point and/or a time of the internally dividing point, from the bio-signal, and may obtain time information and amplitude information corresponding to the time information as characteristic point information related to the pulse waveform components. Further, in order to supplement an unstable bio-signal due to motion noise and the like, the bio-information estimating apparatus may extract, as an additional characteristic point, a time and an amplitude at a point where an amplitude has a maximum value in an SBP interval, or an entire or partial area of the bio-signal.

Then, the bio-information estimating apparatus may extract a feature, to be used for estimating bio-information, by using the obtained characteristic points in 550. In this case, the feature to be used for estimating bio-information may be extracted by combining two or more characteristic points as represented by Equation 3.

Subsequently, the bio-information estimating apparatus may estimate bio-information by using the extracted feature in 560. In this case, a bio-information estimation model may be pre-generated as a function, as represented by Equation 4.

Next, the bio-information estimating apparatus may provide an estimation result of bio-information to a user in 570. In this case, the bio-information estimating apparatus may provide the estimated bio-information to a user by various visual methods using a display, or non-visual methods through voice, tactile sensation, vibration and the like using a speaker, a haptic module, and the like, to a user. Further, the bio-information estimating apparatus may determine a user's health condition based on the estimated bio-information, and may provide guide information, including a warning or measures, to a user based on the determination.

FIGS. 6A to 6E are diagrams explaining an example of a wearable device according to an exemplary embodiment. Various embodiments of the above-described bio-information estimating apparatus may be embedded in a smart watch worn on the wrist or a smart band-type wearable device as described in FIGS. 6A and 6B. However, this is merely exemplary for convenience of explanation, and the wearable device may be applied to an information processing terminal such as a smartphone, a tablet PC, a laptop computer, a desktop computer, and the like.

Referring to FIGS. 6A to 6E, the wearable device 600 includes a main body 610 and a strap 620.

The main body 610 may be formed to have various shapes, and may have modules which are mounted on an inner or outer surface of the main body 610 to perform various functions in addition to the aforementioned function of estimating bio-information. A battery may be embedded in the main body 610 or the strap 620 to supply power to various modules of the wearable device 600.

The strap 620 may be connected to the main body 610. The strap 620 may be flexible, so as to be bent around a user's wrist. The strap 620 may be bent in such a manner that the strap 620 may be detached from the user's wrist or may be formed as a band that is not detachable. Air may be injected into the strap 620 or an airbag may be included in the strap 620, so that the strap 620 may have elasticity according to a change in pressure applied to the wrist, and the change in pressure of the wrist may be transmitted to the main body 610.

A measurer 611, which measures a bio-signal by emitting light onto an object OBJ and by detecting light scattered from the object OBJ, may be mounted at one surface of the main body 610. The measurer 611 may be mounted on a rear surface of the main body 610, i.e., a portion that comes into contact with a user's wrist, and may include one or more light sources 611a for emitting light onto the skin of the wrist, or one or more detectors 611b for detecting light scattered from the object OBJ. The measurer 611 may further include a contact pressure sensor for treasuring contact pressure of the object OBJ.

A processor 612 may be mounted in the main body 610. The processor 612 may be connected to the measurer 611, a communicator 613, a display 614, and various other modules to control operations thereof. In addition, the processor 612 may estimate bio-information by using the bio-signal measured by the measurer 612, and may provide an estimation result to a user through the display 614. As described above, the processor 612 may obtain a characteristic point, related to each pulse waveform component constituting the bio-signal, by using a differential signal of the bio-signal, and may estimate bio-information, such as blood pressure, by using the obtained characteristic point.

In the case where the measurer 611 includes a contact pressure sensor, the processor 612 may monitor a contact state of an object based on the measured contact pressure signal, and may provide a user with a guide to a contact position and/or a contact state through the display 614.

The processor 612 may manage the estimated bio-information, e.g., blood pressure history information, a bio-signal used for measuring blood pressure, and each constituent pulse decomposed from the bio-signal, in a storage device. Further, the processor 612 may generate additional information, including warning information, a health state change trend, and the like, which is used for healthcare management of a user, based on the estimated bio-information, and may manage the generated information in a storage device.

In addition, a manipulator 615, which receives a control command of a user and transmits the received control command to the processor 612, may be mounted in the main body 610. The manipulator 615 may include a power button to input a command to turn on/off the wearable device 600.

The display 614 may be mounted on a front surface of the main body 610 as illustrated therein, and may include a touch panel for touch input. The display 614 may be controlled by the processor 612 to receive a touch input from a user and to transmit the received touch input to the processor 612, and may display a processing result of the processor 612.

Figure 6A:
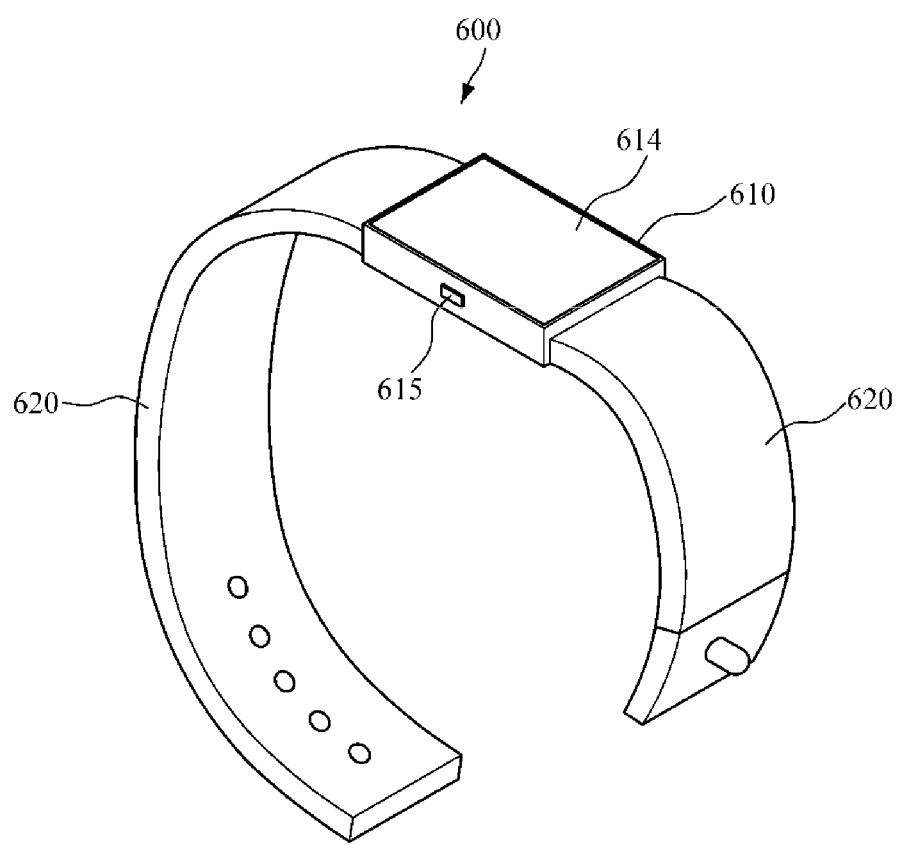
FIGS. 6A to 6E are diagrams explaining an example of a wearable device according to an embodiment.
Figure 6B:
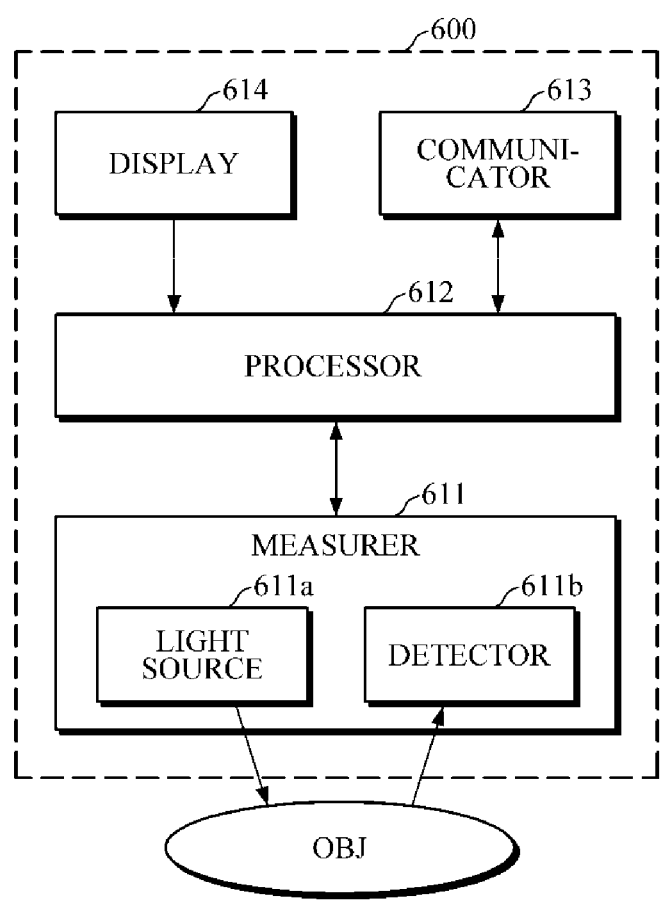
Figure 6C:
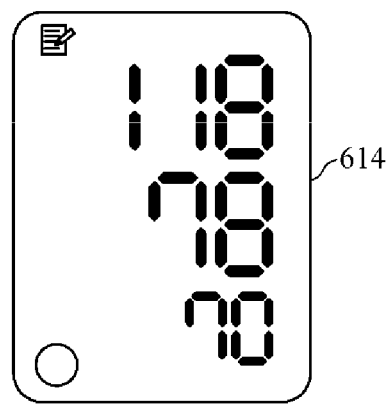
Figure 6D:
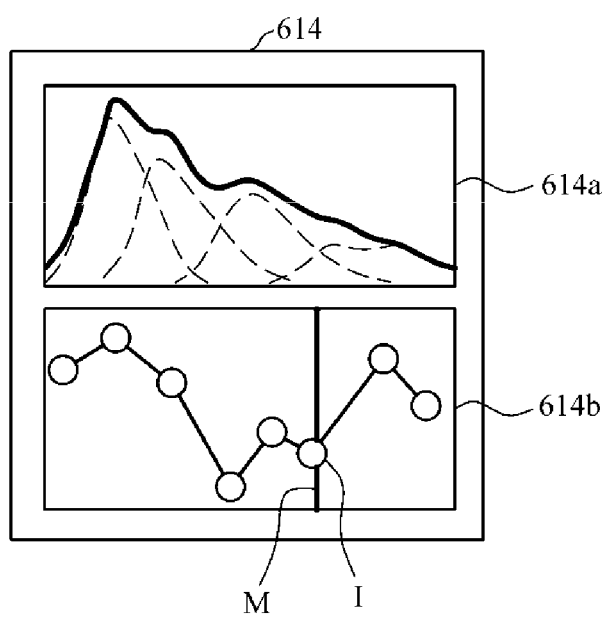
Figure 6E:
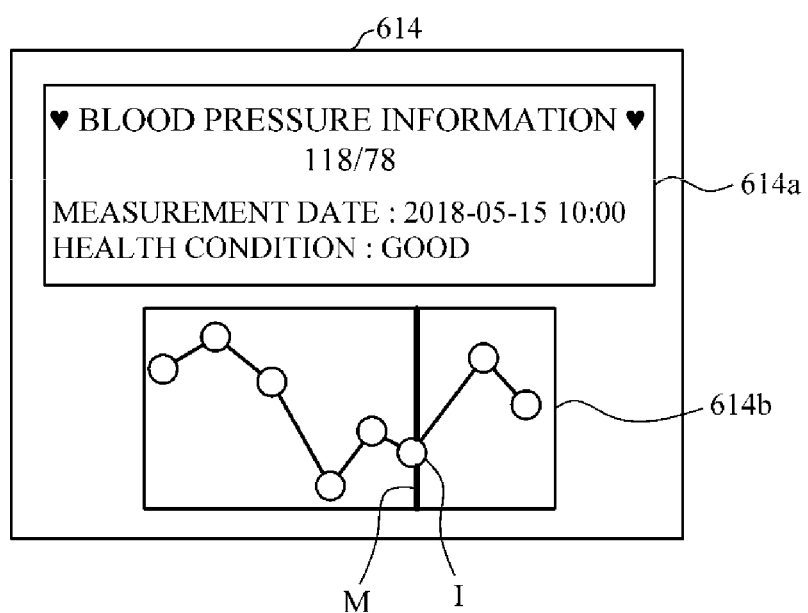

For example, the display 614 may display the estimated bio-information, e.g., blood pressure information, as illustrated in FIG. 6C. In this case, the display 614 may also display additional information such as a warning and the like. When a user requests detailed information by operating the manipulator 615 or by touching the display 614 for touch input, the display 614 may display detailed information by various methods as illustrated in FIGS. 6D and 6E. In this manner, a user may easily identify a blood pressure change trend, and may intuitively understand a bio-signal according to a blood pressure change trend and various types of information extracted from the bio-signal.

Referring to FIGS. 6D and 6E, the display 614 may be divided into a first area 614a and a second area 614b, in which the first area 614a may display detailed information, and the second area 614b may display a blood pressure history graph. In this case, an identification mark M, indicating currently selected blood pressure information I, may be displayed along with the blood pressure history graph. The identification mark M is shown as a vertical line, but is not limited thereto, and may have various shapes such as a circular shape, a polygonal shape such as a square shape, an arrow indicating a position, and the like. When a blood pressure change trend is displayed in the second area 614b, a user may view detailed information of specific blood pressure information by selecting the specific blood pressure information. For example, the user may select the specific blood pressure information by touching the specific blood pressure information of the graph, or by moving the graph to a right side or a left side to place the specific blood pressure information to align with the identification mark M. When a user selects desired blood pressure information in the second area 614b, the display 614 may output information, such as a bio-signal related to the blood pressure information selected in the first area 614a, individual pulse waveform graphs, an estimated blood pressure value at the time point, a measurement date, a health condition at the time point, as illustrated in FIGS. 6D and 6E. However, this is merely exemplary, and may display various types of detailed information not illustrated in FIGS. 6D and 6E.

Moreover, a communicator 613, provided for communication with an external device, such as a mobile terminal of a user, may be mounted in the main body 610. The communicator 613 may transmit an estimation result of bio-information to an external device, e.g., a user's smartphone, to display the result to a user. However, this is merely exemplary, and the communicator 613 may transmit and receive various relevant information.

The disclosure can be implemented as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the disclosure can be easily deduced by one of ordinary skill in the art.

At least one of the components, elements, modules or units described herein may be embodied as various numbers of hardware, software and/or firmware structures that execute respective functions described above, according to an exemplary embodiment. For example, at least one of these components, elements or units may use a direct circuit structure, such as a memory, a processor, a logic circuit, a look-up table, etc. that may execute the respective functions through controls of one or more microprocessors or other control apparatuses. Also, at least one of these components, elements or units may be specifically embodied by a module, a program, or a part of code, which contains one or more executable instructions for performing specified logic functions, and executed by one or more microprocessors or other control apparatuses. Also, at least one of these components, elements or units may further include or implemented by a processor such as a central processing unit (CPU) that performs the respective functions, a microprocessor, or the like. Two or more of these components, elements or units may be combined into one single component, element or unit which performs all operations or functions of the combined two or more components, elements of units. Also, at least part of functions of at least one of these components, elements or units may be performed by another of these components, element or units. Further, although a bus is not illustrated in some of block diagrams, communication between the components, elements or units may be performed through the bus. Functional aspects of the above exemplary embodiments may be implemented in algorithms that execute on one or more processors. Furthermore, the components, elements or units represented by a block or processing steps may employ any number of related art techniques for electronics configuration, signal processing and/or control, data processing and the like.

The foregoing exemplary embodiments are merely exemplary and are not to be construed as limiting. The disclosure can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating bio-information, the apparatus comprising:
   a sensor configured to measure a bio-signal; and
   a processor configured to determine a characteristic point related to a first pulse waveform component and a characteristic point related to an n-th pulse waveform component (n being an integer greater than or equal to 2), the first pulse waveform component and the n-th pulse waveform component constituting the bio-signal, based on a differential signal of the bio-signal, and to estimate bio-information based on the determined characteristic points,
   wherein the processor is further configured to:
      determine an internally dividing point between a first point and a second point related to a specific pulse waveform component in the differential signal, and
      determine a characteristic point related to the specific pulse waveform component based on the determined internally dividing point,
   wherein the processor is further configured to select the first point and the second point based on a sequence of pulse waveform components constituting the bio-signal,
   wherein, in determining the characteristic point related to the first pulse waveform component of the bio-signal, the processor is further configured to select a first local minimum point that firstly appears in the differential signal as the first point, and select any one of adjacent local maximum points preceding or following the first point as the second point,
   wherein, in determining the characteristic point related to the n-th pulse waveform component of the bio-signal, the processor is further configured to respectively select as the first point and the second point, local maximum points respectively preceding and following a second local minimum point that appears n-th in the differential signal, and
   wherein the processor is further configured to, with respect to each of the first pulse waveform component and the n-th pulse waveform component:
      determine a time value of the internally dividing point from the differential signal as a time value of the characteristic point and determine an amplitude value, corresponding to the time value of the internally dividing point, from the bio-signal as an amplitude value of the characteristic point; and
      estimate the bio-information based on the time value and the amplitude value of the characteristic point.

2. The apparatus of claim 1, wherein the processor is configured to determine, as the internally dividing point, a middle point between a time value of the first point and a time value of the second point.

3. The apparatus of claim 1, wherein the processor is configured to apply a weighted value to each of a time value of the first point and a time value of the second point, and determine the internally dividing point based on a result of applying the weighted value.

4. The apparatus of claim 3, wherein the processor is configured to apply the weighted value to each of the time value of the first point and the time value of the second point based on at least one of differential signal strength of each of the first point and the second point, and an amplitude value of the bio-signal which corresponds to each of the time value of the first point and the time value of the second point.

5. The apparatus of claim 1, wherein the processor is configured to, with respect to the first pulse waveform component, determine the internally dividing point between the first point and the second point based on a difference in differential signal strength between the first point and the second point, and a difference in differential signal strength between a third local minimum point, which is different from the first local minimum point and adjacent to the second point, and the second point.

6. The apparatus of claim 1, wherein the processor is configured to extract a feature by combining the determined characteristic points related to the first and the n-th pulse waveform components, and estimate the bio-information based on the extracted feature.

7. The apparatus of claim 1, wherein the sensor comprises:
   a light source configured to emit light onto an object; and
   a detector configured to detect light scattered from the object.

8. The apparatus of claim 1, wherein the bio-information comprises at least one of blood pressure, vascular age, arterial stiffness, aortic pressure waveform, stress index, and degree of fatigue.

9. The apparatus of claim 1, further comprising an output circuit configured to output a processing result of the processor.

10. A method of estimating bio-information, by using an apparatus including a sensor and a processor, the method comprising:
   measuring, using the sensor, a bio-signal;
   determining, by using the processor, a characteristic point related to a first pulse waveform component and a characteristic point related to an n-th pulse waveform component (n being an integer greater than or equal to 2), the first pulse waveform component and the n-th pulse waveform component constituting the bio-signal, based on a differential signal of the bio-signal; and
   estimating, by using the processor, bio-information based on the determined characteristic points,
   wherein the determining the characteristic point related to the first pulse waveform component and the characteristic point related to the n-th pulse waveform component comprises:

determining an internally dividing point between a first point and a second point related to a specific pulse waveform component; and determining a characteristic point related to the specific pulse waveform component based on the determined internally dividing point, wherein the method further comprises selecting the first point and the second point based on a sequence of pulse waveform components constituting the bio-signal, wherein, in determining the characteristic point related to the first pulse waveform component of the bio-signal, a first local minimum point that firstly appears in the differential signal is selected as the first point, and any one of adjacent local maximum points preceding or following the first point is selected as the second point, wherein, in determining the characteristic point related to the n-th pulse waveform component of the bio-signal, local maximum points respectively preceding and following a second local minimum point that appears n-th in the differential signal are respectively selected as the first point and the second point, and wherein the method further comprises, with respect to each of the first pulse waveform component and the n-th pulse waveform component:

determining a time value of the internally dividing point from the differential signal as a time value of the characteristic point and determining an amplitude value, corresponding to the time value of the internally dividing point, from the bio-signal as an amplitude value of the characteristic point; and estimating the bio-information based on the time value and the amplitude value of the characteristic point.

11. The method of claim 10, wherein the determining the internally dividing point comprises:

applying a weighted value to each of a time value of the first point and a time value of the second point; and determining the internally dividing point based on a result of the applying the weighted value.

12. The method of claim 11, wherein the determining the internally dividing point based on the result of the applying the weighted value comprises applying the weighted value to each of the time value of the first point and the time value of the second point based on at least one of a differential signal strength of each of the first point and the second point, and an amplitude value of the bio-signal which corresponds to each of the time value of the first point and the time value of the second point.

13. The method of claim 10, wherein the determining the internally dividing point comprises, with respect to the first pulse waveform component, determining the internally dividing point between the first point and the second point based on a difference in differential signal strength between the first point and the second point, and a difference in differential signal strength between a third local minimum point, which is different from the first local minimum point and adjacent to the second point, and the second point.

14. The method of claim 10, wherein the estimating comprises:

extracting a feature by combining of the determined characteristic points related to the first and the n-th pulse waveform components; and estimating the bio-information based on the extracted feature.

15. The method of claim 10, further comprising outputting an estimation result of the bio-information.

\* \* \* \* \*